US012303383B1

(12) United States Patent
Jin et al.

(10) Patent No.: US 12,303,383 B1
(45) Date of Patent: May 20, 2025

(54) ONE-WAY LIMITING EXPANDABLE ARTIFICIAL BIOLOGICAL HEART VALVE

(71) Applicants: BEIJING BALANCE MEDICAL TECHNOLOGY CO., LTD., Beijing (CN); WEST CHINA HOSPITAL OF SICHUAN UNIVERSITY, Chengdu (CN)

(72) Inventors: Lei Jin, Beijing (CN); Yingqiang Guo, Chengdu (CN); Zhihao Fan, Beijing (CN); Tiegang Liu, Beijing (CN); Jia Wu, Beijing (CN)

(73) Assignees: BEIJING BALANCE MEDICAL TECHNOLOGY CO., LTD., Beijing (CN); WEST CHINA HOSPITAL OF SICHUAN UNIVERSITY, Chengdu (CN)

( * ) Notice: Subject to any disclaimer, the term of this patent is extended or adjusted under 35 U.S.C. 154(b) by 0 days.

(21) Appl. No.: 18/837,848

(22) PCT Filed: Feb. 15, 2023

(86) PCT No.: PCT/CN2023/076279
§ 371 (c)(1),
(2) Date: Aug. 12, 2024

(87) PCT Pub. No.: WO2023/155817
PCT Pub. Date: Aug. 24, 2023

(30) Foreign Application Priority Data

Feb. 15, 2022 (CN) .......................... 202210137462.2

(51) Int. Cl.
*A61F 2/24* (2006.01)
(52) U.S. Cl.
CPC .......... *A61F 2/2412* (2013.01); *A61F 2/2409* (2013.01); *A61F 2220/0041* (2013.01);
(Continued)

(58) Field of Classification Search
CPC .............................. A61F 2/2412; A61F 2/2409
See application file for complete search history.

(56) References Cited

U.S. PATENT DOCUMENTS

2013/0274872 A1* 10/2013 Vesely .................. A61F 2/2412
623/2.17
2019/0321170 A1 10/2019 Green et al.
(Continued)

FOREIGN PATENT DOCUMENTS

| CN | 104884001 A | 9/2015 |
| CN | 105578993 A | 5/2016 |

(Continued)

OTHER PUBLICATIONS

First Office Action dated Aug. 15, 2023 of the counterpart Chinese patent application No. 202310116689.3, which claims priority to CN 202210137462.2.

(Continued)

*Primary Examiner* — Suba Ganesan
(74) *Attorney, Agent, or Firm* — Outlier Patent Attorneys, PLLC

(57) ABSTRACT

The present invention discloses a one-way limiting expandable artificial heart valve which comprises a valve seat (1), a valve leaflet stent (2) and three valve leaflets (3) wherein the valve seat (1) comprises a one-way limiting expandable annular metal seat (4), the annular metal seat (4) is composed of three sections of seat body units (5), the head end of each section of seat body unit (5) is sequentially provided with a first rivet (8), a limiting protrusion (7) and a first long circular groove (6), the tail end of each section of seat body unit (5) is sequentially provided with a second long circular groove (9), a second limiting hole (11) and a first limiting
(Continued)

hole (10), and a second rivet (12), and the artificial heart valve has a normal use original state and a one-way limiting expansion state.

11 Claims, 6 Drawing Sheets

(52) U.S. Cl.
CPC ............... *A61F 2230/0013* (2013.01); *A61F 2250/0003* (2013.01); *A61F 2250/0063* (2013.01)

(56) References Cited

U.S. PATENT DOCUMENTS

| | | | |
|---|---|---|---|
| 2020/0323633 | A1 | 10/2020 | Conklin et al. |
| 2022/0039945 | A1* | 2/2022 | Guttenberg ........... A61F 2/2472 |

FOREIGN PATENT DOCUMENTS

| | | | |
|---|---|---|---|
| CN | 108135699 | A | 6/2018 |
| CN | 112472365 | A | 3/2021 |
| WO | 2012018779 | A2 | 2/2012 |

OTHER PUBLICATIONS

International Search Report of PCT/CN2023/076279 dated Apr. 29, 2023.

\* cited by examiner

ONE-WAY LIMITING EXPANDABLE ARTIFICIAL BIOLOGICAL HEART VALVE

CROSS-REFERENCE TO RELATED APPLICATIONS

This application is a United States National Stage Application filed under 35 U.S.C 371 of PCT Patent Application No. PCT/CN2023/076279, filed Feb. 15, 2023, which claims the priority benefit of Chinese Patent Application No. CN 202210137462.2, filed Feb. 15, 2022, the disclosure of all of which are hereby incorporated by reference in their entirety.

TECHNICAL FIELD

The present invention relates to the field of artificial heart valve, in particular to a one-way limiting expandable artificial biological heart valve.

BACKGROUND ART

According to the United States valve disease treatment guide, foreign artificial biological valves are mainly suitable for valve disease patients above 70 years old, and the vast majority of developed countries, over 75%-80% of patients with valve disease choose to use an artificial heart valve (bovine pericardial valve or porcine aortic valve) for valve replacement surgery; due to the fact that valve calcification easily occurs prematurely after various types of biological valves implanted by valve disease patients below 50 years old in the past, the risk of re-opening heart surgery valve changing is faced, the guide suggests that the valve disease patients below 50 years old select artificial mechanical valves for implanting, and the valve disease patients of 50-70 years old, according to the specific situation of the patient, if there are contraindications to anticoagulation, it is recommended to consider using biological valves. Unlike in the United States, where most patients suffer from degenerative aortic valve disease in the elderly, the majority of valve disease patients in China currently suffer from rheumatic heart valve disease, mainly with mitral valve disease and concurrent multi valve disease. The condition is severe and progresses rapidly, and patients often have to undergo surgical valve replacement at the age of 65 or below. Therefore, domestic patients can only choose artificial mechanical valves. However, patients after mechanical valve surgery need to be anti-coagulated for a long time, and large groups of evidence medical data show that the anti-coagulation-related complications after mechanical valve surgery are the most direct reasons for compromising the postoperative life quality and actual survival rate of these patients, and cannot be solved so far. For a long time, patients with valve disease of about 80% or above in China have been selected to be implanted with artificial mechanical valves, and have always been a helpless choice.

In recent years, with the research and application of the interventional valve-in-valve, it has become practical to input an interventional artificial valve into the previously implanted and damaged biological valve through the catheter, so that these patients can obtain treatment without the risk of opening and changing the valve again. However, due to the limitation of the acquired area of the intra-valve diameter of the damaged valve, only one small size of the interventional valve-in-valve can be accommodated. In many cases, especially for patients with small biological valve numbers implanted for reasons of height or body shape in China, only the small biological valve numbers can be intervened, and clinical data show that the pressure difference across the valves after the small biological valve numbers are used is high, and the durability of the small biological valve numbers is also significantly affected. Therefore, in September 2013, Edwards Life Sciences in the United States disclosed a scalable artificial heart valve under the invention name "Expandable Surgical Heart Valve Construction after Implant" (Application No.: 201380067967.5). The artificial heart valve has an expandable configuration when initially implanted to replace a native valve, such as expansion of an expansion balloon may assume an expanded form. The present invention provides a variety of expandable structures, and the INSPIRIS RESILIA aortic valve has also been formally approved for use in the domestic market by the China National Medical Products Administration in December 2020, as shown in FIG. 1.

In view of the above, the expandable biological valve usually needs to be expanded again when an interventional valve-in-valve is required after being implanted in the body for many years of calcification or damage. Generally, as long as 10~15 years after surgery, if the valve is encapsulated by perivalvular fibroplasia after implantation or calcification occurs in the perivalvular of the preset crackable site, the valve is difficult to expand by the interventional balloon as preset, and according to the practice of extracardiac secondary valvular change surgery, the damaged biological valve cured by perivalvular lesion is difficult to expand again, as shown in FIG. 2.

Therefore, the expansion action in the "Expandable Surgical Heart Valve Construction after Implant" with application Ser. No. 20/138,0067967.5 mentioned earlier is all radial expansion, as shown in FIG. 3, which has the following problems:
  (1) The radial expansion valve seat fully utilizes the radial expansion force of the balloon, and the expansion force required is relatively large, which is difficult to reach or brings a relatively high accident risk in actual operation;
  (2) Due to the complete radial expansion, the tissue generated by the expansion of the valve seat size is larger in the radial expansion portion, and the over-expansion of the valve leaflet root will cause the probability of surrounding conduction block to be greatly increased;

Due to the fact that the expansion demand for surgical artificial valve generally occurs several years after valve implantation, the surrounding tissue of the valve has mostly undergone partial or complete calcification, and the degree of calcification varies from person to person. If radial dilation is fully utilized to dilate calcified tissue at this time, in addition to requiring significant balloon pressure, there is also a risk of the surrounding tissue of the valve being ruptured by calcified lesions (such as the aortic root). At this time, the circumferential shear force not only allows the calcified part to move along the circumference, but also makes it easier to form greater shear force damage to the calcified lesion itself, thereby reducing its stiffness and even being destroyed. These effects are more conducive to reducing the pressure inside the balloon and reducing the impact of calcification on newly implanted valve.

SUMMARY

The present invention provides a one-way limiting expandable artificial heart valve, the original structure and appearance of the one-way limiting expandable artificial heart valve are completely the same as those of a conventional surgically implanted artificial biological heart valve, only after the artificial biological heart valve is implanted for many years, when the artificial biological heart valve is damaged due to valve calcification or other reasons, the artificial biological heart valve can be rotated in one direction along the circumference of the damaged valve by means of the external force of the interventional balloon (shear force), the valve seat units are pushed to be prolonged in sequence in a one-way manner, the diameter of the rotary damaged valve is expanded, and the long circular groove in each seat body unit is designed to in one direction limit and expand the inner diameter of a type of valve opening on the basis of the original structure so as to accommodate an interventional valve-in-valve with the same inner diameter as the original valve opening, so that patients can be better treated, and the later concern of selecting biological valves for most patients in China can be relieved.

The present invention relates to a one-way limiting expandable artificial heart valve prosthesis, the one-way limiting expandable artificial heart valve has two states, the first state of the product is completely the same as the appearance and product performance of artificial biological heart valve products which have been sold for 18 years in the prior enterprise, the difference lies in the structural design as claimed in the above claims, which endows a one-way limiting expandable artificial heart valve with a second state, that is, the one-way limiting expandable artificial heart valve is the same as that in the prior art when all artificial heart valves are implanted into a heart to replace a diseased valve, valve damage occurs due to various reasons in the past after the operation of a patient for many years, when valve treatment in an interventional valve needs to be carried out, the valve can be fed into the damaged valve through an interventional balloon catheter, valve seat units of the limiting expandable artificial heart valve slide and extend in sequence under the action of external force of balloon pressurization, the inner diameter of the valve seat is enlarged along with the precession of the circumference of the valve seat, even if the valve is wrapped or embedded by perivallar tissue lesion, the one-way limiting expandable artificial heart valve can still enter the second state, that is, the valve expands ds the size of one specification, so that the specification size of the valve in the interventional valve input through the catheter is almost the inner mouth area of the original valve, and the patient obtains a better treatment effect.

The specific technical solution of the present invention is: a one-way limiting expandable artificial heart valve, comprising a valve seat, a valve leaflet stent and three valve leaflets attached to the valve leaflet stent, wherein the valve seat comprises a one-way limiting expandable annular metal seat, the annular metal seat is composed of three sections of seat body units connected in a staggered overlapping manner from head to tail end, the head end of each seat body unit is sequentially provided with a first rivet, a limiting protrusion and a first long circular groove, the tail end of each seat body unit is sequentially provided with a second long circular groove matched with the first rivet at the head end of an adjacent seat body unit, a second limiting hole and a first limiting hole matched with the limiting protrusion respectively, and a second rivet matched with the first long circular groove, the first long circular groove of each seat body unit is matched with the second rivet of the adjacent seat body unit and can move in one direction, the second long circular groove of each seat body unit is matched with the first rivet of the adjacent seat body unit and can move in one direction, the limiting protrusion of each seat body unit is matched with the second limiting hole and the first limiting hole of the adjacent seat body unit respectively and can move in one direction, the artificial heart valve has an original state of normal use and a one-way limiting expansion state, and each seat body unit forms the one-way limiting expansion state after synchronous one-way rotation and external expansion.

Among them, the seat body unit may be two or four or more pieces. The head end of each single seat body unit is arranged on the inner side of the tail end of the adjacent seat body unit. Each seat body unit is expanded by no less than 5 atmospheres (atm) balloon, so that the valve seats synchronously rotate in one direction and expand outwards to form the in one-way limiting expansion state, and the original state is the original state of the full-circumference valve annulus structure. Each seat body unit is completely identical in structure, and the head end of each seat body unit is arranged on the inner side or the outer side of the tail end of the adjacent seat body unit. The limiting protrusion is a semicircular protrusion inclined upward along the expansion direction, and the limiting hole has a shape matched with the limiting protrusion. The length of the first and second long circular grooves is consistent with the distance between the two limiting holes. The specification of the three valve leaflets matches the original state. The outer side of the flap seat is coated with a supporting belt composed of a polymeric material, and the supporting belt is matched with an original state. The valve leaflet is modified bovine pericardium, porcine pericardium, porcine aortic valve, flaky animal tissue or non-biosynthetic valve leaflet material. The valve portion composed of the three valve leaflets allows one-way blood flow through the valve portion when the valve portion is in the original configuration. The valve seat is made of Elgiloy alloy, cobalt-chromium alloy, nickel-titanium alloy and implantable stainless steel (316L, cobalt-chromium-nickel-molybdenum-iron alloy). After the valve is in the in one-way limiting expansion state, the original valve fails in function, and the expanded valve seat structure stably accommodates any new valve-interventional valve-in-valve that can be intervened through a catheter. The valve is an aortic valve, a mitral valve or a tricuspid valve. When the valve is an aortic valve, the middle of each seat body unit has a wavy protrusion. When the valve is a mitral valve or a tricuspid valve, a middle portion of an upper side of each seat body unit has a protrusion, and a lower side of each seat body unit is flush.

The one-way limiting expandable artificial heart valve of the present invention is composed of more than two, preferably three identical valve seat units. The three parts are connected head to tail by using the rivet and groove, and are enclosed to form a valve frame structure. When the inner diameter needs to be expanded, the flap seat is radially expanded by using an expansion balloon larger than the inner diameter of the flap seat, and moving parts in the three structures all slide in the same circumferential direction (clockwise or counterclockwise at the same time). Thus, in addition to the radial expansion force generated by the expansion, the surrounding tissue will also be subjected to the shear force generated by the relative displacement tendency generated by the directional rotation of the valve seat and the surrounding tissue.

In contrast, although the prior art patent examples also have the design of sliding and expanding the inner diameter of the valve seat groove, the structural parts do not support sliding in one direction or stretching of the valve support frame, and the expandable surgical heart valve structure of the present invention is mainly subjected to radial expansion force in the peripheral tissue of the expansion process.

The unique advantages of directional rotational dilation of the one-way limiting expandable artificial heart valve in this application, based on the surrounding mechanical and material environment, as well as the impact on the valve annulus or perivalvular tissue in the body, are as follows:

From the surrounding mechanics and material environment and the influence on the in-vivo valve annulus or perivalvular tissue, the advantages of the specific directional rotational expansion of the one-way limiting expandable artificial heart valve of the present application are as follows:

(1) The radially expanded valve seat fully utilizes the balloon radial expansion force, while the directionally rotated valve seat utilizes both the radial expansion force and the circumferential shear force to the surrounding tissue. When the inner diameter expansion size of the same valve seat is reached (for example, the inner diameters are expanded from 23 mm to 25 mm), the balloon internal pressure (radial expansion force) required to directionally rotate the expansion valve seat is smaller;

(2) Since the surrounding tissues generate circumferential extrusion, compared with full radial expansion, the tissue generated by the expansion of the valve seat size is relatively reduced along the radial expansion portion, which can effectively reduce the probability of surrounding conduction block caused by the over-expansion of the valve leaflet root;

(3) Due to the fact that the expansion demand for surgical artificial valve generally occurs several years after valve implantation, the surrounding tissue of the valve has mostly undergone partial or complete calcification, and the degree of calcification varies from person to person. If radial dilation is fully utilized to dilate calcified tissue at this time, in addition to requiring significant balloon pressure, there is also a risk of the surrounding tissue of the valve being ruptured by calcified lesions (such as the aortic root). At this time, the circumferential shear force not only allows the calcified part to move along the circumference, but also makes it easier to form greater shear force damage to the calcified lesion itself, thereby reducing its stiffness and even being destroyed. These effects are more conducive to reducing the pressure inside the balloon and reducing the impact of calcification on newly implanted valve.

Therefore, regardless of the expansion mechanism and the effects generated by the expansion, the one-way limiting expandable artificial heart valve described in the present invention is fundamentally different from the design described in the comparative document in terms of structure and expansion mechanism, and is not covered by any one example in the existing technology.

DRAWING MARK NUMBERS

Figure 1:
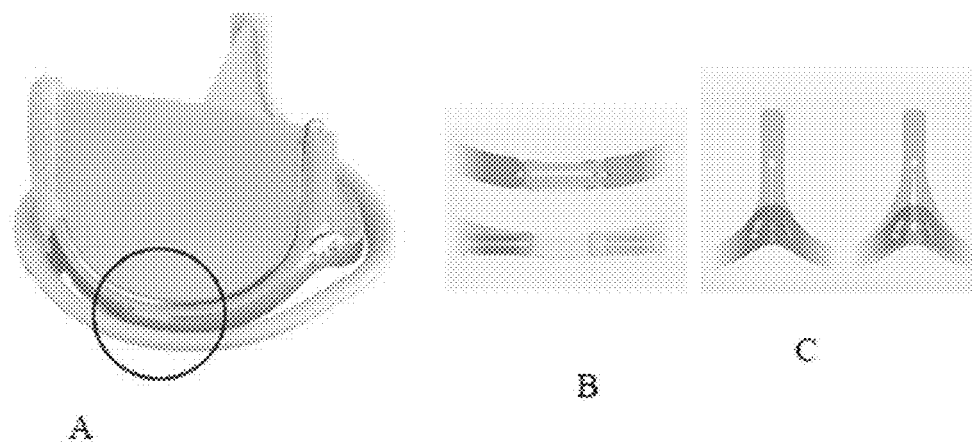
FIGS. 1A-C are schematic diagrams of an expandable valve product of the Edwardt company in the prior art.
Figure 2:
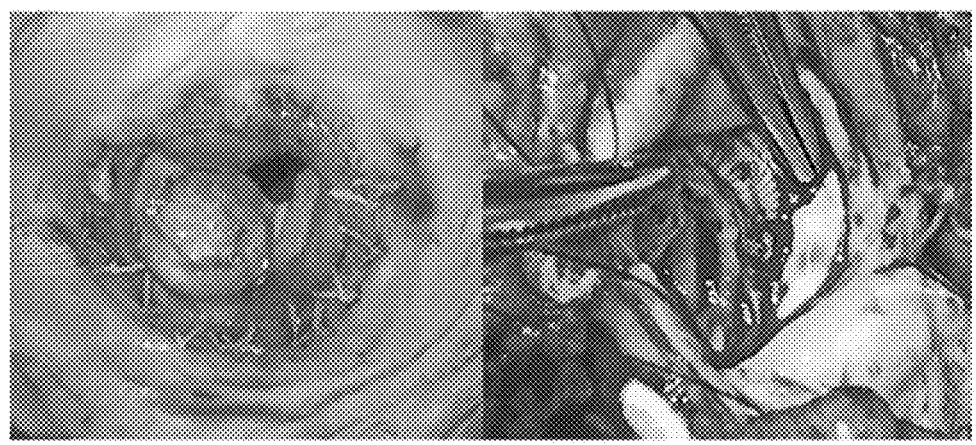
FIG. 2 is a schematic diagram of a damaged biological valve wrapped or cured by a perivalvular lesion.
Figure 3:
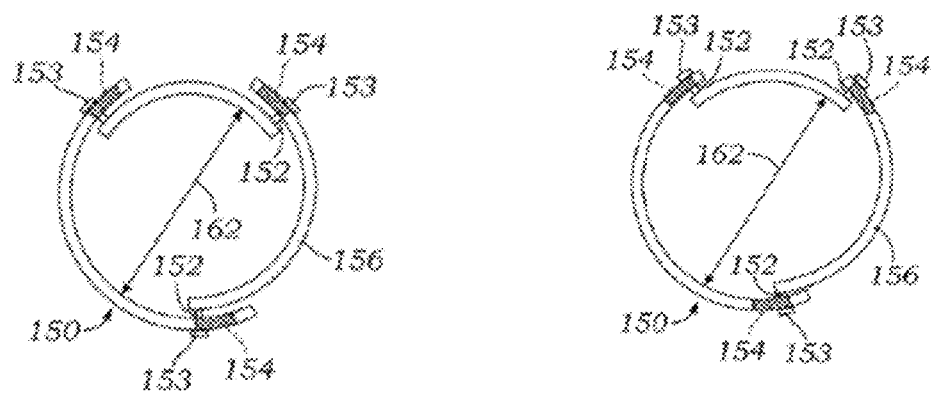
FIG. 3 is a schematic diagram of a valve seat of an expandable valve in the prior art.
Figure 4:
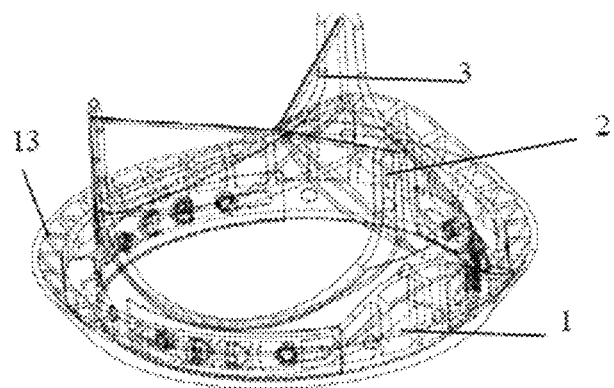
FIG. 4 is a schematic diagram of a one-way limiting expandable artificial biological mitral valve/tricuspid valve according to an example of the present application.
Figure 5:
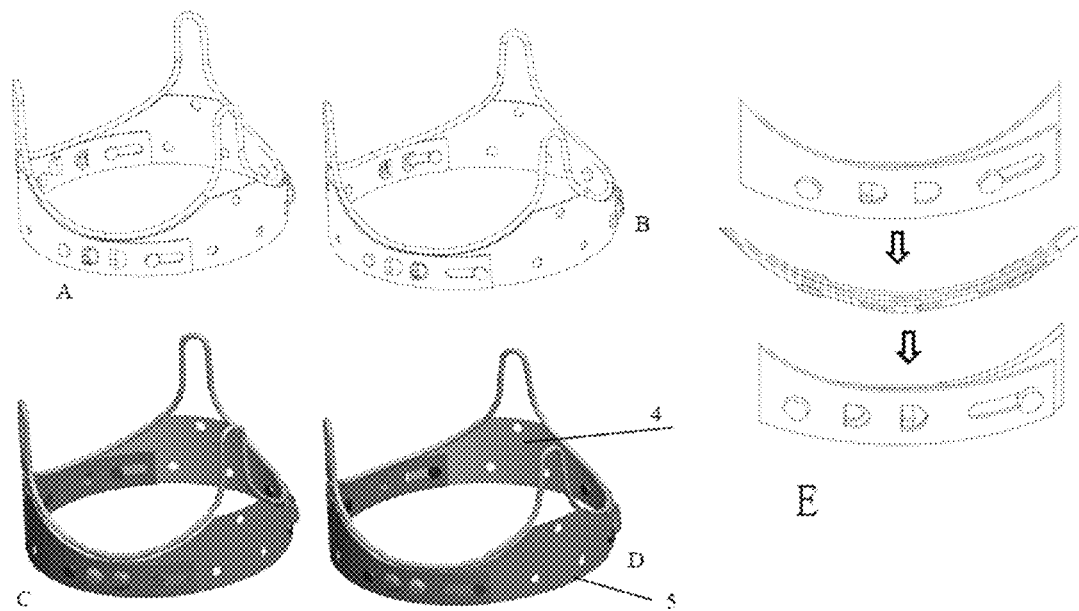
FIGS. 5A-E are schematic diagrams of an original state and an expanded state of the valve seat in FIG. 4.
Figure 6:
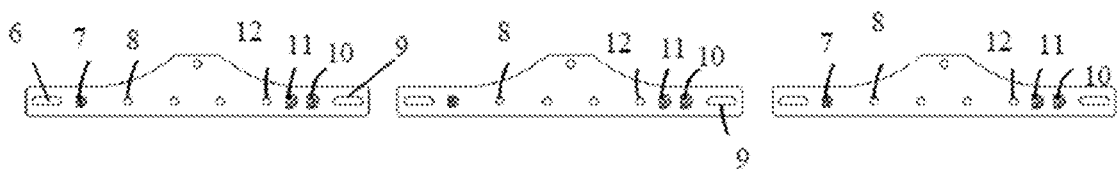
FIG. 6 is an exploded view of the valve seat unit of FIG. 4.
Figure 7:
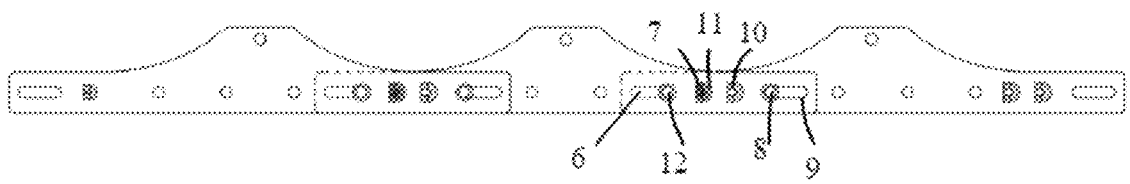
FIG. 7 is an expanded schematic diagram of the valve seat unit of FIG. 4 in an original state.
Figure 8:
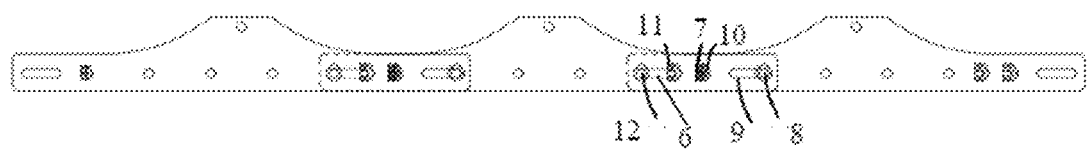
FIG. 8 is an expanded view of the valve seat unit of FIG. 4 in an expanded state.

1: valve seat; 2: valve leaflet stent; 3: valve leaflet; 4: annular metal seat; 5: seat body unit; 6: first long circular groove; 7: limiting protrusion; 8: first rivet; 9: second long circular groove; 10: first limiting hole; 11: second limiting hole; 12: second rivet sleeve; 13: supporting belt.

DETAILED DESCRIPTION

The present invention will be further described in detail below with reference to the accompanying drawings and examples. It should be understood that the specific examples described herein are merely used to explain the present invention, and are not intended to limit the present invention.

Example 1: Schematic Diagram of a one-way Limiting Expandable Artificial Biological Mitral/Tricuspid Valve As shown in FIGS. 4-8, it is a schematic diagram of a one-way limiting expandable artificial biological mitral/tricuspid valve according to the present example. The main structure includes valve seat 1, which is equipped with three valve leaflets 3 through valve leaflet stent 2, which is basically consistent with the structure of common artificial biological mitral valves. The valve seat 1 includes a one-way limiting expandable annular metal seat 4 and a supporting belt 13 wrapped outside the annular metal seat 4.

Among them, the annular metal seat is composed of a seat body unit 5 connected by three overlapping sections of the head and tail ends in inside and outside, wherein the head end of each section of seat body unit 5 is sequentially provided with a first rivet 8, a limiting protrusion 7 and a first long circular groove 6, and the tail end of each section of seat body unit is sequentially provided with a second long circular groove 9, a second limiting hole 11, a first limiting hole 10 and a second rivet 12; when connected to each other, the head end of each seat body unit is inside, and the tail end of each seat body unit is outside; the first long circular groove 6 of each seat body unit is matched with the second rivet 12 of the adjacent seat body unit and can move in one direction; the second long circular groove 9 of each seat body unit is matched with the first rivet 8 of the adjacent seat body unit and can move in one direction; and the semicircular limiting protrusion 7 of each seat body unit is matched with the second limiting hole 10 and the first limiting hole 11 of the adjacent seat body unit respectively and can move in one direction. In the original state, the limiting protrusion 7 is first positioned in the second limiting hole 11, and after one-way limiting expansion, the first rivet and the second anchor are rotated and expanded in the same direction in their respective long circular grooves, and the limiting protrusion 7 is moved displaced to the first limit hole 10 in one direction and positioned here, forming an expansion state, which can be firmly positioned in the expanded state due to the effect of the limiting hole, as shown in FIG. 5E. It should be noted that the setting of the long circular groove and the rivet is not fixed, and the position may be changed according to needs, as long as one-way rotary expansion movement can be performed when the long circular groove and the rivet cooperate with each other.

Figure 9:
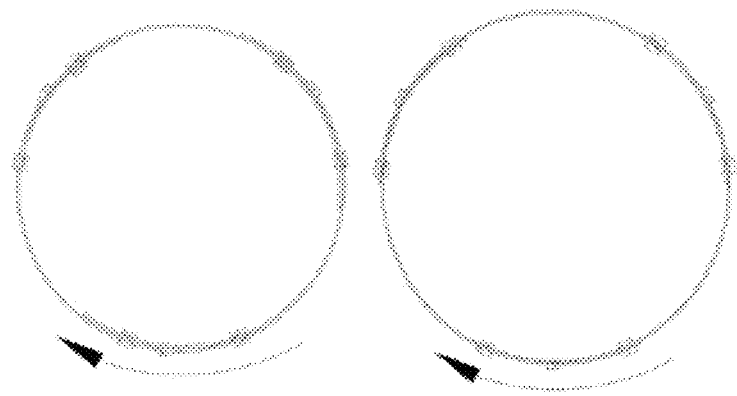
FIG. 9 is a schematic diagram of one-way movement of a seat body unit and limiting expansion of a valve seat diameter.

The artificial heart valve has a normally used original state and a one-way limiting and expanding state, and each seat body unit forms the one-way limiting and expanding state after being synchronously and in one direction rotated and expanded. Each seat body unit is completely identical in structure, and the head end of each seat body unit is arranged on the inner side or the outer side of the tail end of the adjacent seat body unit. The limiting protrusion 7 is a semicircular protrusion inclined upward along the expansion direction, and the limiting hole has a shape matching the limiting protrusion, so that the seat body unit can only rotate in one direction, and it is ensured that the flap seat cannot be restored after expansion. The length of the first long circular groove, the length of the second long circular groove and the distance between the two limiting holes are consistent. The specification of the three valve leaflets matches the original state. The outer side of the flap seat is coated with a supporting belt composed of a polymeric material, and the supporting belt is matched with an original state. The valve leaflet is modified bovine pericardium, porcine pericardium, porcine aortic valve, flaky animal tissue or non-biosynthetic valve leaflet material. The valve portion composed of the three valve leaflets allows one-way blood flow through the valve portion when the valve portion is in the original configuration. The valve seat is made of Elgiloy alloy, cobalt-chromium alloy, nickel-titanium alloy and implantable stainless steel (316L, cobalt-chromium-nickel-molybdenum-iron alloy). After the valve is in the in one-way limiting expansion state, the original valve fails in function, and the expanded valve seat structure stably accommodates any new valve-interventional valve-in-valve that can be intervened through a catheter. The middle of each seat body unit has a wavy protrusion. As shown in FIG. 9, after the valve seat unit is rotated and expanded, the valve seat is expanded and can be implanted into a new valve-in-valve.

In some occasions, the seat body unit of the valve seat can be formed by two symmetrical sections or more than four sections, and can realize the unapplied one-way limiting expandable function.

Example 2: one-way Limiting Expandable Artificial Biological Aortic Valve

Figure 10:
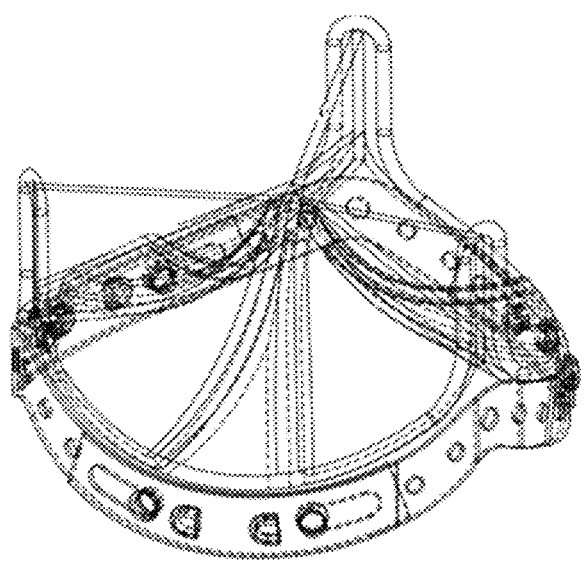
FIG. 10 is a perspective view of a in one direction limiting expandable artificial biological aortic valve according to an example of the present application.
Figure 11:
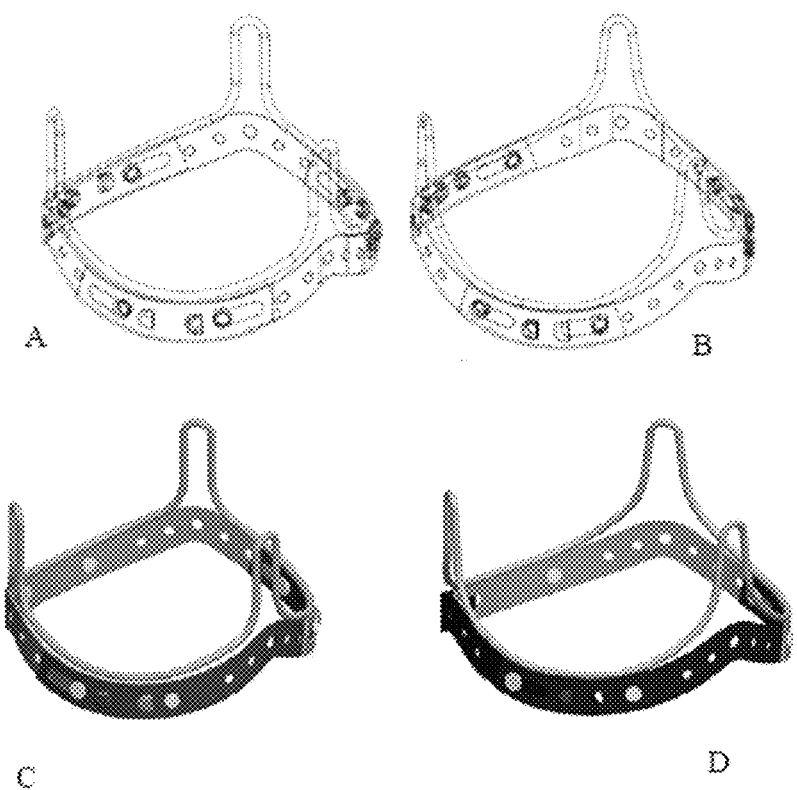
FIG. 11A-D are schematic diagrams of an original state and an expanded state of the valve seat in FIG. 10.

As shown in FIGS. 10-11, it are schematic diagrams of a in one-way limiting expandable artificial biological aortic valve, the structure thereof is basically the same as that of the mitral valve/tricuspid valve of the previous example, and the main difference is that each seat body unit has a wavy protrusion in the middle. As shown in FIG. 11, after the valve seat unit is rotated and expanded, the valve seat is expanded and a new valve-in-valve can be implanted.

In-Vitro Verification

Figure 12:
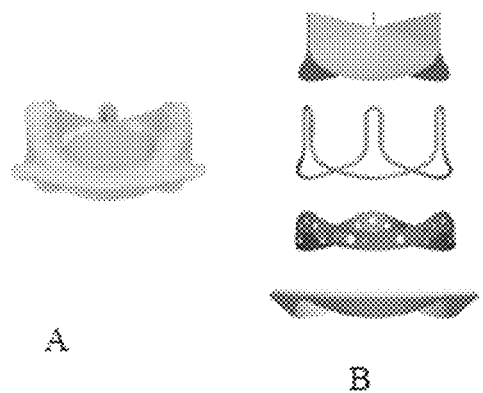
FIG. 12A-B is a combined and exploded schematic diagram of a one-way limiting expandable aortic valve according to an example of the present invention.
Figure 13:
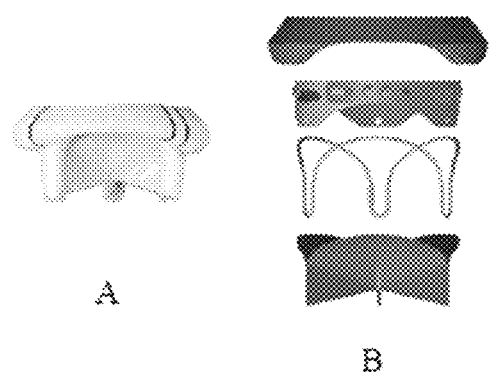
FIG. 13A-B is a combined and exploded schematic diagram of a one-way limiting expandable mitral valve according to an example of the present disclosure.

The present invention relates to a one-way limiting expandable artificial biological heart valve which is divided into an aorta (FIG. 12), a mitral valve (FIG. 13) and a tricuspid valve (the valve seat structure is completely the same as that of the mitral valve). When the interventional balloon is expanded under pressure, whether the aortic valve or the mitral valve or the tricuspid valve, the valve seat unit of the interventional balloon sequentially slides in one direction due to the expansion of the balloon, and the circumference of the valve seat extends to a larger model (FIG. 4), so that the interventional valve-in-valve with the same diameter as the original valve can be accommodated.

In-Vivo Verification

Figure 14:
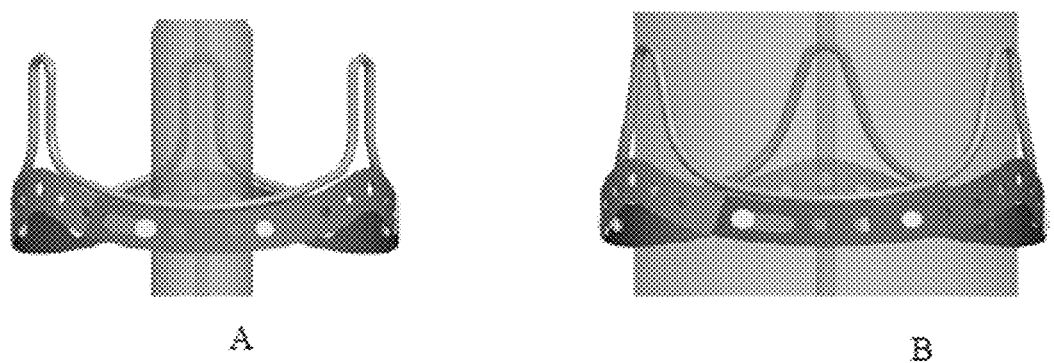
FIG. 14A-B is a pressurized internal expansion of the interventional balloon to accommodate an interventional valve with the same diameter as the original valve.
Figure 15:
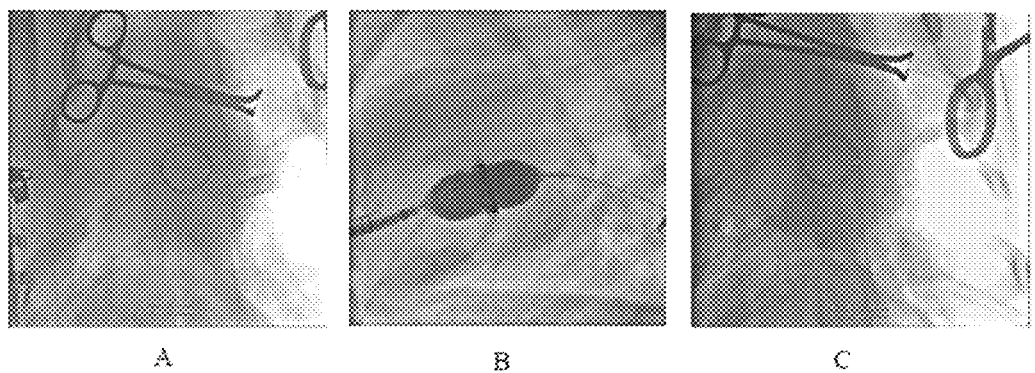
FIGS. 15A-C are schematic diagrams of in-situ implantation of in one-way limiting expandable artificial biological heart valve into experimental animals at different valve positions and measurement of inner diameters before and after expansion.

The present invention provides an in-vivo verification of a one-way limiting expandable artificial biological heart valve. Adult sheep are used as experimental animals, and a one-way limiting expandable artificial biological heart valve is implanted in situ under extracorporeal circulation. Surgical implantation was performed on the aortic valve, mitral valve, and tricuspid valve of the experimental sheep. After 1 day, 3 days, 1 week, 11 weeks and 22 weeks after surgery, the diameter of the implanted valve was accurately measured by DSA angiography (FIG. 14A). Then, the balloon was inserted into the product of the present invention at three different valve positions through the femoral artery, apex puncture, or femoral vein, and a charging pump was connected to pressurize the interventional balloon to expand the product in one direction (FIG. 14B). When the pressure indication reached 5.5 atmospheres, maintain for 5 seconds and then withdraw the pressure, and the valve orifice diameter was measured again and recorded (FIG. 14C).

A total of 41 animal experiments were completed, including 32 animals in the experimental group with mitral valve position, 5 animals in the tricuspid valve position, and 4 animals in the aortic valve position. The corresponding implanted valve specifications are M23, T25, and A21 limited expandable biological valves, respectively. The corresponding sized balloon was used to complete the limited expansion under DSA, all of which could achieve the size specifications of M25, M27, and A23 (FIG. 14D).

The above description is only the preferred examples of the present invention and is not intended to limit the present invention, and any modifications, equivalent substitutions and improvements made within the spirit and principle of the present invention shall be included within the protection scope of the present invention.

The invention claimed is:

1. A one-way limiting expandable artificial heart valve, comprising a valve seat, a valve leaflet stent and three valve leaflets attached to the valve leaflet stent, characterized in that, the valve seat comprises a one-way limiting expandable annular metal seat, the annular metal seat is composed of three sections of seat body units connected in a staggered overlapping manner from head to tail end, the head end of each seat body unit is sequentially provided with a first rivet, a limiting protrusion and a first long circular groove, the tail end of each seat body unit is sequentially provided with a second long circular groove matched with the first rivet at the head end of an adjacent seat body unit, a second limiting hole and a first limiting hole matched with the limiting protrusion respectively, and a second rivet matched with the first long circular groove, the first long circular groove of each seat body unit is matched with the second rivet of the adjacent seat body unit and can move in one direction, the second long circular groove of each seat body unit is matched with the first rivet of the adjacent seat body unit and can move in one direction, the limiting protrusion of each seat body unit is matched with the second limiting hole and the first limiting hole of the adjacent seat body unit respectively and can move in one direction, the artificial heart valve has an original state of normal use and a one-way limiting expansion state, and each seat body unit forms the one-way limiting expansion state after synchronous one-way rotation and external expansion, the limiting protrusion is a semicircular protrusion inclined upward along the expansion direction, the limiting hole has a shape matched with the limiting protrusion, and the length of the first long circular groove, the length of the second long circular groove and the distance between the two limiting holes are consistent, a head end of each single seat body unit is disposed inside a tail end of an adjacent seat body unit, and the valve seat is made of Elgiloy alloy, cobalt-chromium alloy, nickel-titanium alloy, or implantable stainless steel.

2. The one-way limiting expandable artificial heart valve according to claim 1, characterized in that, the seat body unit is two or four or more pieces.

3. The one-way limiting expandable artificial heart valve according to claim 1, characterized in that, each seat body unit is expanded by no less than 5 atmospheric-pressure balloons to enable the valve seat to synchronously rotate in one direction and expand outwards to form the in one-way limiting expansion state, and the original state is an original state of the full-circumference valve annulus structure.

4. The one-way limiting expandable artificial heart valve according to claim 1, characterized in that, the specifications of the three valve leaflets are matched with an original state.

5. The one-way limiting expandable artificial heart valve according to claim 1, characterized in that, the valve seat further comprises a supporting belt composed of a polymeric material, the supporting belt covers the outer side of the annular metal seat, and the supporting belt is matched with an original state.

6. The one-way limiting expandable artificial heart valve according to claim 1, characterized in that, the valve leaflet is modified bovine pericardium, porcine pericardium, porcine aortic valve, flaky animal tissue or non-biosynthetic valve leaflet material.

7. The one-way limiting expandable artificial heart valve according to claim 1, characterized in that, the valve portion composed of the three valve leaflets allows one-way blood flow through the valve portion when the valve portion is in the original state.

8. The one-way limiting expandable artificial heart valve according to claim 1, characterized in that, after the valve is in the in one-way limiting expansion state, the original valve fails in function, and the expanded valve seat structure stably accommodates any new valve interventional valve-in-valve that can be intervened through a catheter.

9. The one-way limiting expandable artificial heart valve according to claim 1, characterized in that, the valve is an aortic valve, a mitral valve or a tricuspid valve.

10. The one-way limiting expandable artificial heart valve according to claim 1, characterized in that, when the valve is an aortic valve, a middle portion of each seat body unit has a wavy protrusion.

11. The one-way limiting expandable artificial heart valve according to claim 1, characterized in that, when the valve is a mitral valve or a tricuspid valve, a middle portion of an upper side of each seat body unit has a protrusion, and a lower side of each seat body unit is flush.

* * * * *